(12) United States Patent
Cella

(10) Patent No.: US 6,191,276 B1
(45) Date of Patent: Feb. 20, 2001

(54) METHOD FOR PREPARING STERICALLY HINDERED PHOSPHORAMIDATES

(75) Inventor: James Anthony Cella, Clifton Park, NY (US)

(73) Assignee: General Electric Company, Schenectady, NY (US)

( * ) Notice: Under 35 U.S.C. 154(b), the term of this patent shall be extended for 0 days.

(21) Appl. No.: 09/511,561

(22) Filed: Feb. 23, 2000

Related U.S. Application Data

(60) Provisional application No. 60/135,755, filed on May 25, 1999.

(51) Int. Cl.⁷ .............................. C07D 241/04; C07F 9/22
(52) U.S. Cl. .............................. 544/337; 558/138; 564/14
(58) Field of Search .............................. 558/138; 564/14; 544/337

(56) References Cited

U.S. PATENT DOCUMENTS 3,937,765 * 2/1976 Toy et al. .............................. 260/973
5,973,041 * 10/1999 Campbell et al. .................... 524/117

FOREIGN PATENT DOCUMENTS 10175985   6/1998   (JP) .

OTHER PUBLICATIONS

John J. Talley, "Preparation of Sterically Hindered Phosphoramidates", J. Chem. Engr. Data, vol. 33, pp. 221–222, 1988.

\* cited by examiner

Primary Examiner—Mukund J. Shah
Assistant Examiner—Venkataraman Balasubramanian
(74) Attorney, Agent, or Firm—S. Bruce Brown; Noreen C. Johnson

(57) ABSTRACT

Sterically hindered phosphoramidates such as N,N'-bis[di-(2,6-xylenoxy)phosphoryl]piperazine are prepared by the reaction of a sterically hindered diaryl chlorophosphate, such as di-(2,6-xylyl) chlorophosphate, with a basic nitrogen compound containing at least two basic N-H groups, preferably a heterocyclic compound such as piperazine, in the presence of calcium oxide as an acid acceptor. The reaction is conducted in the presence of at least one dipolar aprotic solvent.

14 Claims, No Drawings

METHOD FOR PREPARING STERICALLY HINDERED PHOSPHORAMIDATES

CROSS-REFERENCE TO RELATED APPLICATIONS

This application claims priority from provisional application Ser. No. 60/135,755 filed May 25, 1999.

BACKGROUND OF THE INVENTION

This invention relates to the preparation of phosphoramidates, and more particularly to their preparation from nitrogen bases and diaryl chlorophosphates.

The use of sterically hindered phosphoramidates such as N,N'-bis[di-(2,6-xylenoxy)phosphoryl]piperazine (hereinafter sometimes "XPP") as flame retardant additives for synthetic resins, especially thermoplastic resins such as polycarbonates, ABS resins and blends thereof, has been discovered to have particular advantages including improved high temperature stability of the resulting blends. Reference is made, for example, to U.S. Pat. No. 5,973,041 and to copending, commonly owned applications Ser. Nos. 09/235,679 and 09/364,915.

XPP and analogous compounds may be conveniently prepared by the reaction of a diaryl chlorophosphate, such as di-(2,6-xylyl) chlorophosphate, with a heterocyclic compound containing two basic N-H groups, such as piperazine. According to the prior art as illustrated by Talley, *J. Chem. Eng. Data*, 33, 221–222 (1983), this reaction is conducted in chloroform as solvent, in the presence of triethylamine as an acid acceptor. The triethylamine is employed in stoichiometric amount or in excess, and reacts with the by-product hydrogen chloride to drive the reaction to completion.

The Talley paper describes the preparation of a number of analogous compounds including those derived from such nitrogen compounds as benzylamine, cyclohexylamine, aniline, ethylenediamine and p-phenylenediamine as well as piperazine. Reported yields were as high as 90% for the reaction with aniline, and as low as 61% for the reaction with p-phenylenediamine. Piperazine afforded XPP in a yield of only 68%, one of the lowest reported.

If the use of XPP as a flame retardant additive is to be commercially feasible, it is necessary to improve its yield by a significant amount. Also, it is desirable to minimize the use of the relatively toxic solvent chloroform and stoichiometric amounts of triethylamine on a commercial scale.

It is of interest, therefore, to develop high-yield methods employing relatively harmless materials for the preparation of XPP and analogous compounds.

SUMMARY OF THE INVENTION

The present invention is based on the discovery that a relatively inexpensive basic inorganic compound, calcium oxide, may be employed as an acid acceptor in the preparation of XPP and analogous compounds, provided at least one dipolar aprotic solvent is employed entirely or in part. When so employed, product yield is high and the reaction is rapid.

Accordingly, in one embodiment the invention is a method for preparing a sterically hindered phosphoramidate which comprises contacting a sterically hindered diaryl chlorophosphate with a basic nitrogen compound containing at least two basic N-H groups in the presence of calcium oxide as an acid acceptor and at least one dipolar aprotic solvent.

In another embodiment the invention is a method for preparing a phosphoramidate which comprises contacting a diaryl chlorophosphate with a basic nitrogen compound containing at least two basic N-H groups in the presence of calcium oxide as an acid acceptor and at least one dipolar aprotic solvent, said phosphoramidate having a glass transition temperature of at least about 0° C., preferably of at least about 10° C., and most preferably of at least about 20° C.

DETAILED DESCRIPTION; PREFERRED EMBODIMENTS

Within the context of the present invention a sterically hindered phosphoramidate is one in which at least one aryl substituent linked to heteroatom-phosphorus has at least one substituent on the aryl ring ortho to the aryl-heteroatom-phosphorus linkage. The sterically hindered diaryl chlorophosphates employed in the method of this invention include those having the formula (I)

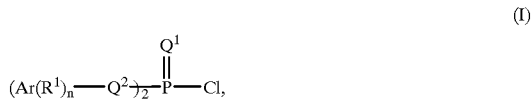

wherein Ar is an aromatic group, each $R^1$ is independently alkyl, aryl or halo, $Q^1$ is oxygen of sulfur, $Q^2$ is oxygen, sulfur, or $NR^1$, and n has the value of 1 up to the number of free valency sites on the aromatic ring and at least one $R^1$ substituent on the aryl ring is ortho to the heteroatom-phosphorus linkage. Preferably, Ar is a phenyl ring and n has the value of 1–5. Preferably, each $R^1$ is $C_{1-4}$ primary or secondary alkyl; most preferably, methyl, and n is 2 with each substituent ortho to the phosphorus linkage. Thus, preferred chlorophosphates are di-(2,4,6-trimethylphenyl) chlorophosphate and di-(2,6-dimethylphenyl) chlorophosphate, also known as di-(2,6-xylyl) chlorophosphate.

Any compound, acyclic or cyclic, containing at least two basic N-H groups may be employed. Suitable compounds include those of the formula

wherein each $R^2$ is a $C_{1-4}$ primary or secondary alkyl radical or both $R^2$ radicals taken together are ethylene. Illustrative acyclic compounds are N,N'-dimethylethylenediamine and N,N'-diethylethylenediamine. Heterocyclic compounds are generally preferred; they are illustrated by piperazine and 1,2,3,4-tetrahydroquinoxaline, both unsubstituted and substituted. Piperazine is most preferred.

In a preferred embodiment, the method of the invention may be used to produce a phosphoramidate having a glass transition temperature of at least about 0° C., preferably of at least about 10° C., and most preferably of at least about 20° C. In particular, the method of the invention may be used to produce a phosphoramidate of the formula III:

(III)

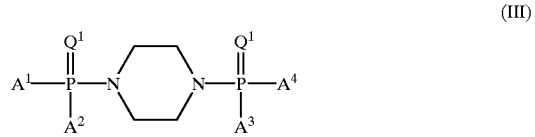

wherein each $Q^1$ is independently oxygen or sulfur; and each of $A^{1-4}$ is independently an alkyloxy, alkylthio, aryloxy, or arylthio residue, or an aryloxy or arylthio residue containing at least one alkyl or halogen substitution, or mixture thereof; or an amine residue. In an especially preferred embodiment of the invention, each $Q^1$ is oxygen, and each $A^{1-4}$ moiety is a 2,6-dimethylphenoxy moiety or a 2,4,6-trimethylphenoxy moiety. These phosphoramidates are piperazine-type phosphoramidates. In the above formula wherein each $Q^1$ is oxygen, and each $A^{1-4}$ moiety is a 2,6-dimethylphenoxy moiety, the glass transition temperature of the phosphoramidate is about 62° C. and the melting point is about 192° C.

In another preferred embodiment, the method of the invention may be used to produce a phosphoramidate having a glass transition temperature of at least about 0° C., preferably of at least about 10° C., and most preferably of at least about 20° C., of the formula IV:

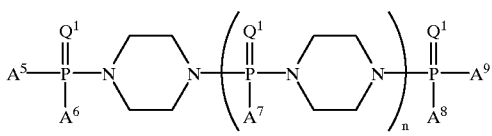

(IV)

wherein each $Q^1$ is independently oxygen or sulfur; and each of $A^{5-9}$ is independently an alkyloxy, alkylthio, aryloxy, or arylthio residue, or an aryloxy or arylthio residue containing at least one alkyl or halogen substitution, or mixture thereof; or an amine residue; and n is from 0 to about 5. In a more preferred embodiment, each $Q^1$ is oxygen, and each $A^{5-9}$ moiety is independently phenoxy, 2,6-dimethylphenoxy, or 2,4,6-trimethylphenoxy, and n is from 0 to about 5.

In another embodiment the method of the invention may be used to produce a phosphoramidate having a glass transition temperature of at least about 0° C., preferably of at least about 10° C., and most preferably of at least about 20° C., of the formula V:

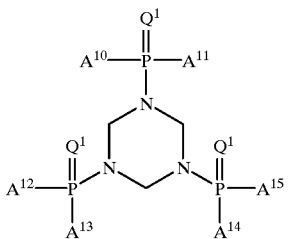

(V)

wherein each $Q^1$ is independently oxygen or sulfur; and each of $A^{10-15}$ is independently an alkyloxy, alkylthio, aryloxy, or arylthio residue, or an aryloxy or arylthio residue containing at least one alkyl or halogen substitution, or mixture thereof; or an amine residue. In a more preferred embodiment, each $Q^1$ is oxygen, and each $A^{10-15}$ moiety is independently phenoxy, 2,6-dimethylphenoxy, or 2,4,6-trimethylphenoxy.

In another embodiment the method of the invention may be used to produce a phosphoramidate having a glass transition temperature of at least about 0° C., preferably of at least about 10° C., and most preferably of at least about 20° C., of the formula VI:

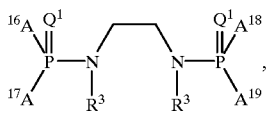

(VI)

wherein each $Q^1$ is independently oxygen or sulfur; each of $A^{16-19}$ is independently an alkyloxy, alkylthio, aryloxy, or arylthio residue, or an aryloxy or arylthio residue containing at least one alkyl or halogen substitution, or mixture thereof; or an amine residue; and each $R^3$ is an alkyl radical, or both $R^3$ radicals taken together are an alkylidene or alkyl-substituted alkylidene radical. In a preferred embodiment, each $Q^1$ is oxygen; both $R^3$ radicals taken together are an unsubstituted $(CH_2)_m$ alkylidene radical, wherein m is 2 to 10; and each $A^{16-19}$ moiety is independently phenoxy, 2,6-dimethylphenoxy, or 2,4,6-trimethylphenoxy. In a more preferred embodiment, each $Q^1$ is oxygen; each $R^3$ is methyl; and each $A^{16-19}$ moiety is independently phenoxy, 2,6-dimethylphenoxy, or 2,4,6-trimethylphenoxy.

In another embodiment the method of the invention may be used to produce a phosphoramidate having a glass transition point of at least about 0° C., preferably of at least about 10° C., and most preferably of at least about 20° C., of the formula VII:

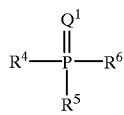

(VII)

wherein $Q^1$ is oxygen or sulfur, and $R^4$ is of the formula VIII:

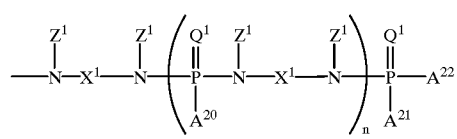

(VIII)

wherein each $Q^1$ is independently oxygen or sulfur; each of $A^{20-22}$ is independently an alkyloxy, alkylthio, aryloxy, or arylthio residue, or an aryloxy or arylthio residue containing at least one alkyl or halogen substitution, or mixture thereof; or an amine residue; each $Z^1$ is an alkyl radical, aromatic radical, or aromatic radical containing at least one alkyl or halogen substitution or mixture thereof; each $X^1$ is an alkylidene radical, aromatic radical, or aromatic radical containing at least one alkyl or halogen substitution or mixture thereof; n is from 0 to about 5; and $R^5$ and $R^6$ are each independently an alkyloxy, alkylthio, aryloxy, or arylthio residue, or an aryloxy or arylthio residue containing at least one alkyl or halogen substitution, or mixture thereof; or an amine residue. In a preferred embodiment, each $Q^1$ is oxygen; each $A^{20-22}$ moiety is independently phenoxy, 2,6-dimethylphenoxy, or 2,4,6-trimethylphenoxy; each $Z^1$ is methyl or benzyl; each $X^1$ is an alkylidene radical containing 2–24 carbon atoms; n is from 0 to about 5; and $R^5$ and $R^6$ are each independently phenoxy, 2,6-dimethylphenoxy, or 2,4,6-trimethylphenoxy.

In another embodiment the method of the invention may be used to produce a phosphoramidate having a glass transition point of at least about 0° C., preferably of at least about 10° C., and most preferably of at least about 20° C., of the formula IX:

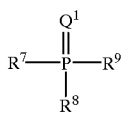

(IX)

wherein $Q^1$ is oxygen or sulfur; and $R^7$ is of the formula X:

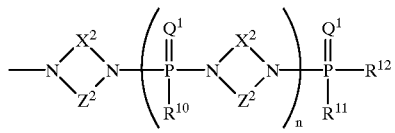

(X)

wherein each $Q^1$ is independently oxygen or sulfur; each $X^2$ is an alkylidene or alkyl-substituted alkylidene residue, aryl residue, or alkaryl residue; each $Z^2$ is an alkylidene or alkyl-substituted alkylidene residue; each of $R^{10}$, $R^{11}$, and $R^{12}$ is independently an alkyloxy, alkylthio, aryloxy, or arylthio residue, or an aryloxy or arylthio residue containing at least one alkyl or halogen substitution, or mixture thereof; or an amine residue; n is from 0 to about 5; and $R^8$ and $R^9$ are each independently an alkyloxy, alkylthio, aryloxy, or arylthio residue, or an aryloxy or arylthio residue containing at least one alkyl or halogen substitution, or mixture thereof; or an amine residue. In a preferred embodiment, each $Q^1$ is oxygen; each $X^2$ is an alkylidene or alkyl-substituted alkylidene residue; each $Z^2$ is an alkylidene or alkyl-substituted alkylidene residue; each of $R^8$, $R^9$, $R^{10}$, $R^{11}$, and $R^{12}$ is independently phenoxy, 2,6-dimethylphenoxy, or 2,4,6-trimethylphenoxy; and n is from 0 to about 5. In a more preferred embodiment, each $Q^1$ is oxygen; each $X^2$ and $Z^2$ is independently an unsubstituted alkylidene residue of the form $(CH_2)_m$, wherein m is 2 to 10; each of $R^8$, $R^9$, $R^{10}$, $R^{11}$, and $R^{12}$ is independently phenoxy, 2,6-dimethylphenoxy, or 2,4,6-trimethylphenoxy; and n is from 0 to about 5. In an especially preferred embodiment, the phosphoramidate is derived from piperazine (i.e. $X^2$ and $Z^2$ are each —CH$_2$—CH$_2$—).

In another preferred embodiment, the method of the invention may be used to produce a cyclic phosphoramidate having a glass transition point of at least about 0° C., preferably of at least about 10° C., and most preferably of at least about 20° C. of the formula XI:

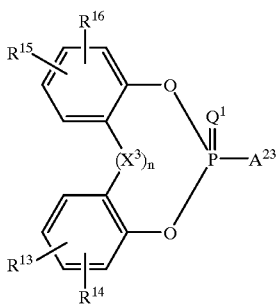

(XI)

wherein each of $R^{13-16}$ is independently a hydrogen or an alkyl radical, $X^3$ is an alkylidene radical, $Q^1$ is oxygen or sulfur, and $A^{23}$ is a group derived from a primary or secondary amine having the same or different radicals that can be aliphatic, alicyclic, aromatic, or alkaryl, or $A^{23}$ is a group derived from a heterocyclic amine, or $A^{23}$ is a hydrazine compound. Preferably $Q^1$ is oxygen. It should be noted that when n is 0, then the two aryl rings are linked together at that site (i.e. where $X^3$ is absent) by a single bond in the positions ortho,ortho' to the phosphoryl bonds.

In another preferred embodiment, the method of the invention may be used to produce a bis(cyclic) phosphoramidate having a glass transition point of at least about 0° C., preferably of at least about 10° C., and most preferably of at least about 20° C. of the formula XII:

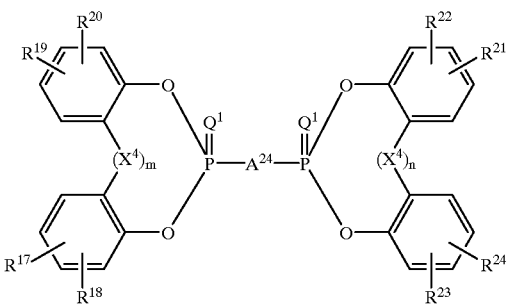

(XII)

wherein $Q^1$ is oxygen or sulfur; each of $R^{7-24}$ is independently a hydrogen or an alkyl radical; $X^4$ is an alkylidene radical; m and n are each independently 0 or 1, and $A^{24}$ is

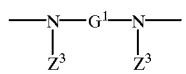

wherein $G^1$ is sulfur, an alkylidene radical, alkyl-substituted alkylidene radical, aryl radical, or alkaryl radical, and each $Z^3$ is independently an alkyl radical, an aryl radical, or an aryl radical containing at least one alkyl or halogen substitution, or mixture thereof; or wherein $A^{24}$ is

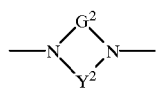

wherein $G^2$ is alkylidene, aryl, or alkaryl, and $Y^2$ is alkylidene or alkyl-substituted alkylidene. Preferred phosphoramidates are those wherein $Q^1$ is oxygen, $A^{24}$ is a residue of piperazine, and the phosphoramidate has a plane of symmetry through $A^{24}$. Highly preferred phosphoramidates include those wherein $Q^1$ is oxygen, $A^{24}$ is a residue of piperazine; the phosphoramidate has a plane of symmetry through $A^{24}$; at least one R substituent on each aryl ring is a methyl adjacent to the oxygen substituent; n and m are each 1; and $X^4$ is $CHR^{25}$ wherein $R^{25}$ is a hydrogen or an alkyl residue of from about 1 to about 6 carbon atoms. It should be noted that when either or both of m or n is 0, then the two aryl rings are linked together at that site (i.e. where $X^4$ is absent) by a single bond in the positions ortho,ortho' to the phosphoryl bonds.

The method may also be used to make phosphoramidates with intermediate glass transition temperatures by using a mixture of various substituted and non-substituted aryl moieties within the phosphoramidate.

According to the invention, the acid acceptor and solvent which may be employed for preparation of the phosphoramidate are calcium oxide and a dipolar aprotic solvent, as illustrated by dimethylformamide, dimethylacetamide, dimethyl sulfoxide, sulfolane, hexamethylphosphoramide, and N-methylpyrrolidinone. Dimethylformamide is generally the preferred dipolar aprotic solvent, by reason of its relatively low cost. Other solvents, including, but not limited to, chloroform, dichloromethane, or toluene, may be used in admixture with the dipolar aprotic solvent and their presence is sometimes beneficial from the standpoint of yield. It is preferred that water be excluded from the reaction mixture.

The method of the invention is typically conducted at temperatures in the range of about 20–100° C., preferably about 20–60° C. An inert atmosphere, such as nitrogen or argon, is preferably employed. Various methods of blending the reagents may be employed. Preferably, the acid acceptor, solvent and basic nitrogen compound are introduced in sequence, or all three ar e introduced together. When a catalyst is employed, it may accompany the other reagents or may be added subsequently.

Molar ratios of diary chlorophosphate to b asic nitrogen compound are generally in the range of about 2.0–2.5:1, preferably about 2.05–2.2:1. Calcium oxide is present in at least stoichiometric amount for use as an acid acceptor, i.e., a molar ratio of calcium oxide to diaryl chiorophosphate in the range of about 0.5–1.0:1 since calcium is divalent. The dipolar aprotic solvent typically constitutes about 15–100% by volume of total solvent.

The progress of the reaction ma y be monitored by art-recognized analytical methods. In general, a reaction time on the order of 0.5–15 hours is adequate for the reaction to progress to effective completion. The phosphormidate may then be isolated by conventional operations.

Product yields affor ded by the invention are generally comparable to those obtained by the use of triethylamine as an acid acceptor, as known in the art.

The invention is illustrated by the following examples.

EXAMPLE 1

A 50 milliliter (ml) three-necked flask equipped with a mechanical stirrer and condenser connected to a nitrogen bubbler was charged in a nitrogen atmosphere, with 860 milligrams (mg) (10 millimoles [mmol]) of piperazine, 560 mg (10 mmol) of anhydrous calcium oxide, 50 mg of o-terphenyl (internal standard) and 20 ml of dry dimethylformamide. Stirring was commenced while 6.20 grams (g) (20 mmol) of di-(2,6-xylyl) chilorophosphate was added at once. The reaction mixture was sampled periodically until no change in product composition was noted. A 70.3% yield of XPP was obtained.

A control reaction run using triethylamine as the base gave a 70.2% yield of XPP.

EXAMPLE 2

The flask of Example 1 was charged, in a nitrogen atmosphere, with 860 mg (10 mmol) of piperazine, 0.560 mg (10 mmol) of anhydrous calcium oxide, 50 mg of o-terphenyl (internal standard) and 20 ml of dry chloroform. Stirring was commenced while 6.20 g (20 mmol) of di-(2, 6-xylyl) chlorophosphate was added at once. The reaction mixture was stirred for 3 hours, at which time a 16% conversion to XPP was observed. Dimethylformamide, 5 ml, was then added and the mixture was stirred an additional 30 minutes. Analysis then showed production of XPP in 80.4% yield.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a sterically hindered phosphoramidate which comprises contacting a sterically hindered diaryl chlorophosphate with a basic nitrogen compound containing at least two basic N-H groups in the presence of calcium oxide as an acid acceptor and at least one solvent which is dipolar aprotic, optionally in combination with a second solvent which is not dipolar artic, wherein the diaryl chlorophosphate has the formula

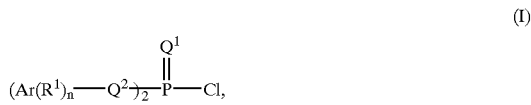

wherein Ar is an aromatic group, each $R^1$ is independently alkyl, aryl or halo, $Q^1$ is oxygen or sulfur, $Q^2$ is oxygen, sulfur, or $NR^1$, and n has the value of 1 up to the number of free valency sites on the aromatic ring and at least one $R^1$ substituent on the aryl ring is ortho to the heteroatom-phosphorus linkage; and wherein the basic nitrogen compound has the formula

wherein each $R^2$ is a $C_{1-4}$ primary or secondary alkyl radical or both $R^2$ radicals taken together are ethylene or a benzene ring with nitrogens attached in the 1,2 positions; and wherein the dipolar aprotic solvent is dimethylformamide, dimethylacetamide, dimethyl sulfoxide or N-methylpyrrolidinone.

2. A method according to claim 1, wherein Ar is phenyl, $Q^1$ and $Q^2$ are each oxygen, n is 2 or 3, and $R^1$ is methyl.

3. A method according to claim 1 wherein the basic nitrogen compound is piperazine or 1,2,3,4-tetrahydroquinoxaline.

4. A method according to claim 1 wherein another solvent is also present.

5. A method according to claim 4 wherein the other solvent is chloroform.

6. A method according to claim 1 wherein contact is effected at a temperature in the range of about 20–100° C. in an inert atmosphere.

7. A method according to claim 1 wherein the molar ratio of diaryl chlorophosphate to basic nitrogen compound is in the range of about 2.0–2.5:1.

8. A method according to claim 1 wherein the molar ratio of calcium oxide to diaryl chlorophosphate is in the range of about 0.5–1.0:1.

9. A method according to claim 1 wherein the dipolar aprotic solvent is present in an amount in the range of about 15–100% by volume of total solvent.

10. A method for preparing a phosphoramidate which comprises contacting a diaryl chlorophosphate with a basic nitrogen compound containing at least two basic N-H groups in the presence of calcium oxide as an acid acceptor and at least one solvent which is dipolar aprotic, optionally in combination with a second solvent which is not dipolar aprotic, wherein the diaryl chlorophosphate has the formula

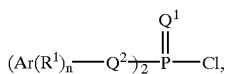 (I)

wherein Ar is an aromatic group, each $R^1$ is independently alkyl, aryl or halo, $Q^1$ is oxygen or sulfur, $Q^2$ is oxygen, sulfur, or $NR^1$, and n has the value of 1 up to the number of free valency sites on the aromatic ring and at least one $R^1$ substituent on the aryl ring is ortho to the heteroatom-phosphorus linkage; and wherein the basic nitrogen compound has the formula

wherein each $R^2$ is a $C_{1-4}$ primary or secondary alkyl radical or both $R^2$ radicals taken together are ethylene or a benzene ring with nitrogens attached in the 1,2 positions; and wherein the dipolar aprotic solvent is dimethylformamide, dimethylacetamide, dimethyl sulfoxide or N-methylpyrrolidinone;

said phosphoramidate having a glass transition temperature of at least about 0° C.

11. The method of claim 10 in which the phosphoramidate has a glass transition temperature of at least about 10° C.

12. The method of claim 10 in which the phosphoramidate has a glass transition temperature of at least about 20° C.

13. A method for preparing N,N'-bis[di-(2,6-xylyl)phosphoryl]piperazine which comprises contacting di-(2,6-xylyl) chlorophosphate with piperazine in the presence of calcium oxide as an acid acceptor and dimethylformamide as solvent.

14. A method for preparing N,N'-bis[di-(2,6-xylyl)phosphoryl]piperazine which comprises contacting di-(2,6-xylyl) chlorophosphate with piperazine in the presence of calcium oxide as an acid acceptor and a mixture of dimethylformamide and chloroform as solvent.

* * * * *

UNITED STATES PATENT AND TRADEMARK OFFICE
CERTIFICATE OF CORRECTION

PATENT NO. : 6,191,276 B1
DATED : February 20, 2001
INVENTOR(S) : James Anthony Cella It is certified that error appears in the above-identified patent and that said Letters Patent is hereby corrected as shown below:

Title page,
Item [57], ABSTRACT,
Line 2, the term "(2,6-xylenoxy)phosphoryl]piperazine" should read -- (2,6-xylyl) phosphoryl]piperazine --.

Column 1,
Line 14, the term "N,N'-bis[di-(2,6-xylenoxy)phosphoryl]piperazine" should read -- N, N'-bis[di-(2,6-xylyl)phosphoryl]piperazine --.

Column 2,
Line 26, the phrase "of sulfur" should read -- or sulfur --.

Column 3,
Line 61, the single word "trimethylphenoxy." on this line should be deleted.

Column 6,
Line 30, the phrase "of $R^{7-24}$" should read -- of $R^{17-24}$ --.

Column 7,
Line 22, the word "diary" should read -- diaryl --.
Line 26, the word "chiorophosphate" should read -- chlorophosphate --.
Line 33, the word "phosphormidate" should read -- phosphoramidate --.
Line 48, the word "chilorophosphate" should read -- chlorophosphate --.
Line 58, the number "0.560 mg." should read -- 560 mg. --.

UNITED STATES PATENT AND TRADEMARK OFFICE
CERTIFICATE OF CORRECTION

PATENT NO. : 6,191,276 B1
DATED : February 20, 2001
INVENTOR(S) : James Anthony Cella It is certified that error appears in the above-identified patent and that said Letters Patent is hereby corrected as shown below:

<u>Column 8,</u>
Line 15, the word "artic" should read -- aprotic --.

Signed and Sealed this

Thirteenth Day of August, 2002

Attest:

Attesting Officer

JAMES E. ROGAN
*Director of the United States Patent and Trademark Office*